US012702406B2

(12) United States Patent
Kam et al.

(10) Patent No.: US 12,702,406 B2
(45) Date of Patent: Aug. 11, 2026

(54) IMPLANT AND SUTURE ORGANIZATION DEVICE

(71) Applicant: CONMED CORPORATION, Utica, NY (US)

(72) Inventors: Andrew Kam, Odessa, FL (US); Andrew Draybuck, Tampa, FL (US)

(73) Assignee: CONMED CORPORATION, Utica, NY (US)

( * ) Notice: Subject to any disclaimer, the term of this patent is extended or adjusted under 35 U.S.C. 154(b) by 0 days.

(21) Appl. No.: 18/786,684

(22) Filed: Jul. 29, 2024

(65) Prior Publication Data

US 2024/0389999 A1 Nov. 28, 2024

Related U.S. Application Data

(62) Division of application No. 18/132,660, filed on Apr. 10, 2023, now Pat. No. 12,048,430, which is a division of application No. 16/460,044, filed on Jul. 2, 2019, now Pat. No. 11,622,762.

(51) Int. Cl.
*A61B 17/06* (2006.01)
*B65D 73/00* (2006.01)

(52) U.S. Cl.
CPC .... *A61B 17/06133* (2013.01); *B65D 73/0078* (2013.01); *A61B 2017/06142* (2013.01)

(58) Field of Classification Search
CPC ...... A61B 2017/0414; A61B 17/06138; A61B 2017/06152; A61B 17/06116; A61B 2017/06142; A61B 17/06133; B65D 73/0078
USPC .................................... 206/63.3, 784, 380
See application file for complete search history.

(56) References Cited

U.S. PATENT DOCUMENTS 4,063,638 A * 12/1977 Marwood ........ A61B 17/06138 206/363
4,496,045 A * 1/1985 Ferguson ......... A61B 17/06138 206/476
4,574,957 A * 3/1986 Stead .............. A61B 17/06138 206/388
5,121,836 A * 6/1992 Brown ............ A61B 17/06138 206/63.3
5,390,782 A * 2/1995 Sinn ................ A61B 17/06138 206/380

(Continued)

*Primary Examiner* — Chun Hoi Cheung
(74) *Attorney, Agent, or Firm* — Bond, Schoeneck & King, PLLC; Frederick J.M. Price

(57) ABSTRACT

An organization device for maintaining a suspensory graft fixation device (i.e., an implant and suture) in a desired position. The device includes a substrate having top and bottom edges with first and second panels extending therebetween. The device also includes a first central longitudinal axis extending in a direction from the top edge to the bottom edge between the first and second panels. The first and second panels are foldable about the axis between open and closed positions. The device also includes an opening extending through the bottom edge and into the first panel, and a plurality of top slits and bottom slits. The plurality of top slits includes at least one top slit which is aligned with the first opening. The device additionally includes a tabs adjacent the opening. The slits and tabs are configured to maintain suture of a suspensory graft fixation device in an organized manner.

6 Claims, 15 Drawing Sheets

(56) References Cited

U.S. PATENT DOCUMENTS 5,566,821 A * 10/1996 Brown ............. A61B 17/06138 206/388
5,788,063 A * 8/1998 Van Ness ......... A61B 17/06138 206/380
5,871,089 A * 2/1999 Odermatt ......... A61B 17/06138 206/227
5,896,982 A * 4/1999 Surcin .............. A61B 17/06138 206/784
6,029,805 A * 2/2000 Alpern ............. A61B 17/06138 206/388
6,080,184 A * 6/2000 Peters .............. A61B 17/06133 606/228
6,260,696 B1 * 7/2001 Braginsky ........ A61B 17/06133 206/380
6,409,016 B1 * 6/2002 Braginsky ........ A61B 17/06119 206/397
8,091,321 B2 * 1/2012 Malinowski ..... A61B 17/06138 53/430
2002/0175091 A1 * 11/2002 Williamson, IV ........................... A61B 17/06138 206/227
2017/0172570 A1 * 6/2017 Wentling ............. B65D 5/4266

* cited by examiner 1100
1102
1104
1106
1108
1110
1112
1114
1116
1120
1130
1132
1134
1136
1140

IMPLANT AND SUTURE ORGANIZATION DEVICE

CROSS-REFERENCE TO RELATED APPLICATIONS

The present application is a division of U.S. Non-Provisional application Ser. No. 18/132,660 filed on Apr. 10, 2023, which is a division of U.S. Non-Provisional application Ser. No. 16/460,044, now U.S. Pat. No. 11,622,762, filed on Jul. 2, 2019, the entireties of which is incorporated herein by reference.

BACKGROUND OF THE INVENTION

1. Field of the Invention

The present invention is directed generally to an organization device and, more particularly, to a foldable substrate for maintaining a surgical implant and suture in a desired position.

2. Description of Related Art

The repair and reconstruction of torn or damaged soft tissues is a common surgical procedure. For example, replacement graft ligaments may be secured at the site of the original ligament. The procedure generally involves drilling bone tunnels into adjacent bones at the site of the original ligament and securing a graft ligament within these bone tunnels. In many applications, such as in the knee joint, such procedures may be performed arthroscopically. The graft ligament may be an autograft, an allograft, a xenograft, or it may be totally artificial and synthetic. Common types of anterior cruciate ligament (ACL) grafts, for example, include ones which may be autologous or allograft bone-patellar tendon-bone or soft tissue (such as semitendinosus and gracilis tendons), both types harvested by techniques well known to those skilled in the art.

The graft ligaments may be secured within the bone tunnels in a variety of ways. Of prime importance is the degree to which the graft ligaments can withstand pullout forces prior to complete healing. For example, it is known to use interference screws inserted parallel to the tunnel axis to compress the ends of the graft ligament against the wall of the bone tunnel to secure the graft ligament and promote tissue in-growth.

Suspensory graft fixation devices have been developed to secure a graft ligament in a bone tunnel. One such device is described in U.S. Pat. No. 8,852,250 (Lombardo et al.), entitled Graft Fixation Implant, assigned to the assignee hereof and incorporated by reference in its entirety herein. Suspensory graft fixation devices work by lying transversely across the opening of a bone tunnel and generally take the form of an elongated anchor member which suspends a graft retaining loop from a fixation point on the surface of a bone to which the graft is to be attached (in this case, a femur). The elongated member has an axis and a pair of suture receiving apertures symmetrically situated on the axis on opposite sides of the center of the elongated member. In ACL procedures, the elongated member, often called a button, is adapted to be situated transversely across the exit opening of the bone tunnel on the lateral femoral cortex so that a supporting loop, generally made of suture material, can be suspended from the button and can extend into the bone tunnel from the suture receiving apertures of the button. The suture loop supports one end of a graft ligament passed through the loop.

The term "suture" as used herein may be any type of filamentous material such as a biocompatible or bioabsorbable filament, ribbon, tape, woven or non-woven material capable of providing the loop support and the frictional resistance required by the device described herein.

In many instances, the suture and/or suture loops of suspensory graft fixation devices become entangled or twisted prior to use. In the event of entanglement or twisting, the surgeon must spend additional time returning the suture and/or suture loops back to the original configuration, which is then suitable for proper loading of a graft.

Therefore, there is a need for a device for maintaining a suspensory graft fixation device (i.e., an implant and suture) in a desired position.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety (ies).

SUMMARY OF THE INVENTION

Embodiments of the present invention are directed to an organization device for maintaining a suspensory graft fixation device (i.e., an implant and suture) in a desired position. According to one aspect, the present invention is an implant and suture organization device. The organization device includes, but is not limited to, a substrate having a top edge and a bottom edge with a first panel and a second panel extending therebetween. The organization device also includes a first central longitudinal axis extending in a direction from the top edge to the bottom edge between the first panel and the second panel. The first panel and the second panel are foldable about the first central longitudinal axis between an open position and a closed position. The organization device also includes an opening extending through the bottom edge and into the first panel, a plurality of top slits extending into the top edge of the first panel. The plurality of top slits includes a central top slit which is aligned with at least a portion of the first opening. The organization device additionally includes a plurality of bottom slits extending into the bottom edge of the first panel, a first tab on the first panel adjacent a first side of the opening, and a second tab on the first panel adjacent a second side of the opening. The first tab and the second tab both open toward the opening.

According to another aspect, the present invention is an organization system. The system includes a substrate having a top edge and a bottom edge with a first panel and a second panel extending therebetween. The system additionally includes, but is not limited to, a central longitudinal axis extending in a direction from the top edge to the bottom edge between the first panel and the second panel. The first panel and the second panel are foldable about the central longitudinal axis between an open position and a closed position. The system additionally includes an opening extending through the bottom edge and into the first panel and a central top slit extending into the top edge of the first panel. The central top slit is aligned with at least a portion of the opening. The system also includes a first tab on the first panel adjacent a first side of the first opening and a second tab on the first panel adjacent a second side of the first opening. The first tab and the second tab both open toward the first opening. The system additionally includes a suspensory graft fixation device having an anchor body with a suture woven therethrough, creating a loop of the suture extending from a side of the anchor body and two limbs of the suture extending from an opposing side of the anchor body. The loop is wrapped around the first tab and the second tab such that a bottom of the loop extends across the opening. The two limbs extend to and through the central top slit.

According to another aspect, the present invention is a method for securing a suspensory graft fixation device in an organized configuration. The method includes, but is not limited to, the steps of: (i) providing an organization device comprising a substrate having a top edge and a bottom edge with a first panel and a second panel extending therebetween, a central longitudinal axis extending in a direction from the top edge to the bottom edge between the first panel and the second panel, an opening extending through the bottom edge and into the first panel, a plurality of top slits extending into the top edge of the first panel, a central top slit of the plurality of top slits aligned with at least a portion of the opening, a plurality of bottom slits extending into the bottom edge of the first panel, a first tab on the first panel adjacent a first side of the first opening, a second tab on the first panel adjacent a second side of the first opening; (ii) providing a suspensory graft fixation device having an anchor body with a suture woven therethrough, creating a loop extending from a side of the anchor body and two limbs extending from an opposing side of the anchor body; (iii) wrapping the loop around the first tab and the second tab such that a bottom of the loop extends across the first opening; and (iv) pulling the two limbs to and through the central top slit.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
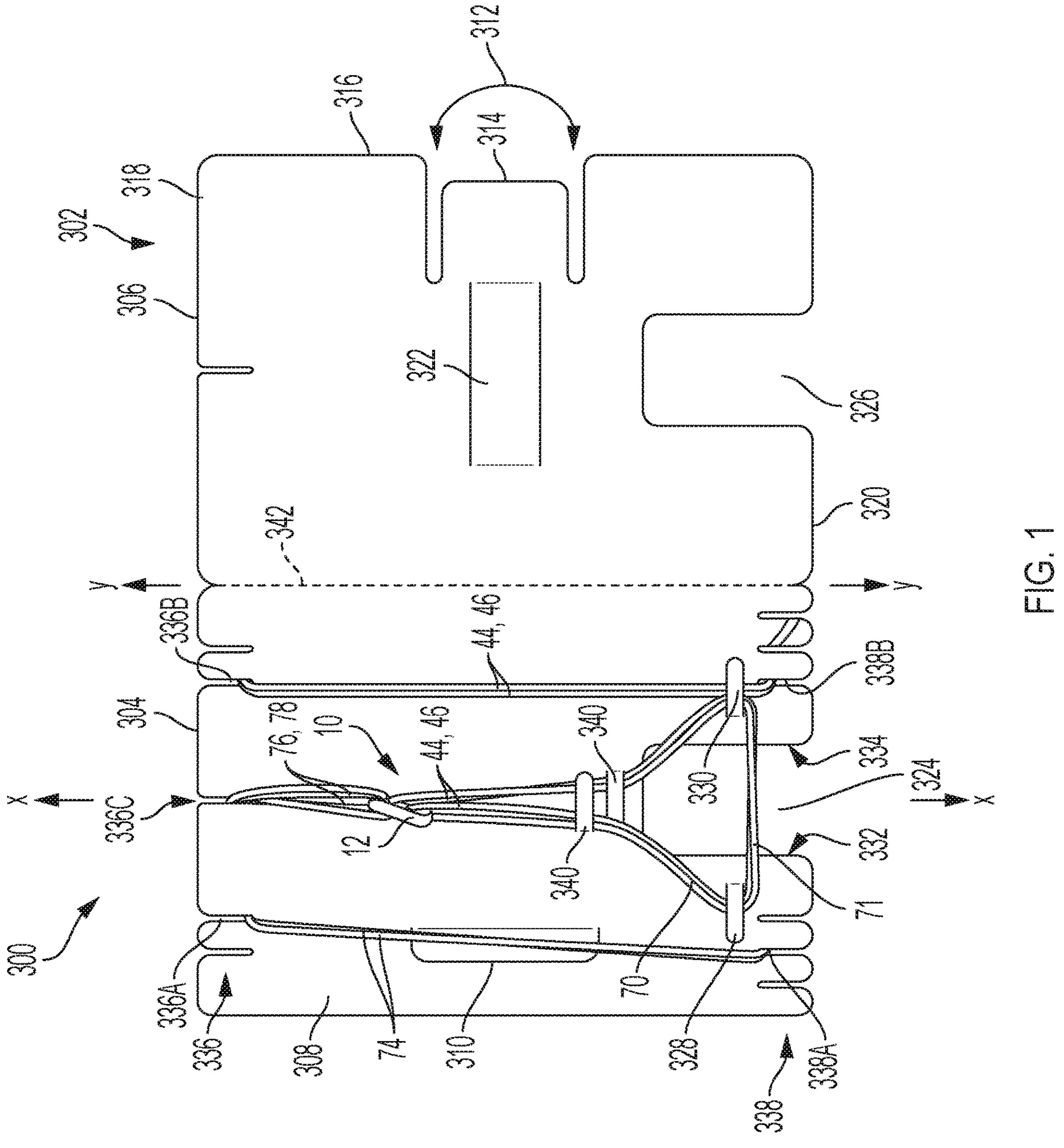
FIG. 1 is a perspective view schematic representation of an implant and suture organization device in an open position, according to an embodiment.

Referring now to the figures, wherein like reference numerals refer to like parts throughout, FIG. 1 shows a perspective view schematic representation of an implant and suture organization device 300 in an open position, according to an embodiment. In the depicted embodiment, the organization device 300 comprises a substrate 302 having a first panel 304 and a second panel 306 with a central longitudinal y-y axis extending therebetween. The term "central" is used herein to describe a longitudinal axis separating the first panel 304 from the second panel 306 and does not necessarily require longitudinal y-y axis be substantially centered between the first panel 304 and the second panel 306. The substrate 302 can be any suitable material that is lightweight yet firm for transportation. For example, the substrate 302 can be composed of high density polyethylene (HDPE).

A first side 308 of the first panel 304 is shown in FIG. 1. The first side 308 of the first panel 304 comprises a locking slit 310. In the depicted embodiment, the locking slit 310 is substantially parallel to the central longitudinal y-y axis. The second panel 306 comprises a pair of spaced cutouts 312 (or grooves), creating a protrusion 314 (or large tab) on a side 316 of the second panel 306 between a top edge 318 of the substrate 302 and a bottom edge 320 of the substrate 302. The protrusion 314 is sized and configured to fit within the locking slit 310 in the first panel 304. Additionally, the first side 308 of the substrate 302 comprises a retainer band 322. In the depicted embodiment, the retainer band 322 is on the second panel 306. The retainer band 322 can be a separate, additional material added to the second panel 306 or the retainer band 322 can be formed in the second panel 306 via a pair of parallel cuts. The purpose of the retainer band 322 is to retain a feature or device therein, as described in further detail below. The orientation of each of these elements (e.g., locking slit 310, spaced cutouts 312, protrusion 314) can be orientated in any number of ways/directions ("up," "down," at an angle), so long as they cooperate with each other as described herein (as should be understood by a person of skill in the art in conjunction with a review of this disclosure).

As shown in FIG. 1, the first panel 304 of the organization device 300 comprises a first opening 324 extending through its bottom edge 320. The second panel 306 of the organization device 300 comprises a second opening 326 extending through its bottom edge 320. In the depicted embodiment, the first opening 324 and the second opening 326 are equidistant from the central longitudinal y-y axis (although, one or both can be positioned anywhere along the bottom edge). In the embodiment shown in FIG. 1, the first opening 324 and the second opening 326 are rectangular and extend into at least a portion of the first panel 304 and into at least a portion of the second panel 306, respectively. However, other shapes, sizes, and configurations for the first and second openings 324, 326 can be used.

Still referring to FIG. 1, the first panel 304 comprises a first tab 328 and a second tab 330 adjacent the first opening 324. In the depicted embodiment, the first tab 328 is adjacent a first side 332 of the first opening 324 and the second tab 330 is adjacent an opposing, second side 334 of the first opening 324. The first tab 328 opens toward the first opening 324 and the second tab 330 opens in the opposing direction, also toward the first opening 324, as shown. As described later, the first and second tabs 328, 330 are used to maintain an implant and suture in a desired configuration.

FIG. 1 additionally shows that the organization device 300 comprises a plurality of top slits 336 extending into the top edge 318 of the first panel 304. In the depicted embodiment, the top edge 318 comprises five top slits 336. Specifically, there is one central top slit 336C aligned with a central longitudinal x-x axis extending through the first opening 324 and a set of two peripheral top slits 336A, 336B on either side of the central top slit 336C. As also shown in FIG. 1, the organization device 300 comprises a plurality of bottom slits 338 extending into the bottom edge 320 of the first panel 304. In the depicted embodiment, some of the bottoms slits 338A are adjacent the first side 332 of the first opening 324 and some of the bottom slits 338B are adjacent the second side 334 of the first opening 324. In FIG. 1, the organization device 300 has three bottom slits 338A adjacent the first side 332 of the first opening 324 and three bottom slits 338B adjacent the second side 334 of the first opening 324. The top slits 336 and the bottom slits 338 are used to maintain an implant and suture in a desired position. Accordingly, any number of top slits 336 and bottom slits 338 can be used, depending on the type of implant or suture to be arranged in the organization device 300. Side slits could also be used and implemented in a similar manner as described herein.

The organization device 300 may have additional tabs for positioning the implant and suture. In the embodiment shown in FIG. 1, the organization device 300 comprises one or more intermediary tabs 340. The intermediary tabs 340 are positioned between the first opening 324 and the top edge 318 of the first panel 304. In the depicted embodiment, there are two intermediary tabs 340, opening in opposing directions. The intermediary tabs 340 are positioned between the first opening 324 and the top edge 318 of the first panel 304 such that the central longitudinal x-x axis extends therethrough.

As shown in FIG. 1 and mentioned above, the organization device 300 is configured to hold an implant and/or suture in a desired position. FIGS. 3-8, show various view schematic representations of an exemplary embodiment of an implant with suture. In the embodiment shown in FIGS. 3-8, the implant (and suture) is a suspensory graft fixation device 10, such as that taught in U.S. Pat. No. 9,931,197 issued on Apr. 3, 2018, and incorporated herein by reference. Other implants with sutures (as should be understood by a person of ordinary skill in the art in conjunction with a review of this disclosure) can be used in conjunction with the organization device 300.

The suspensory graft fixation device 10 includes, but is not limited to, an elongated anchor member 12 and suture in the form of filamentous strand 40. The suspensory graft fixation device 10 can include, but are not limited to, other details described herein below. For example, the anchor member 12 can have a first end 14, a second end 16, an axis 18, and a pair of suture receiving apertures 20, 22. The anchor member 12 can have a top surface 24 and a bottom surface 26 (best seen in FIG. 6). The apertures 20, 22 are situated on opposite sides of a central bridge portion 28 extending between them. In the preferred embodiment, the apertures 20, 22 are formed in a pocket/recess 30 set in top surface 24 of the anchor member 12. The recess 30 has a perimeter 32 at the intersection of the recess 30 with the top surface 24, the purpose of which will be explained later. The anchor member 12 also has a suture return aperture 34 extending between the top and bottom surfaces 24, 26 as well as a pulling aperture 36. While there could be one return aperture for each suture limb, in the preferred embodiment, both limbs pass through one return aperture.

The suspensory graft fixation device 10 is designed to have the anchor member 12 operate with a filamentous strand 40 suitable for following a tortuous path through the various apertures of anchor member 12. For example, in the preferred embodiment, the filamentous strand 40 is a single length of appropriately sized suture. The term "suture" as used herein may be used interchangeably with "filamentous material" and, as described above, will be understood to mean any biocompatible or bioabsorbable strand of material which can, when combined with the anchor member 12, operate to support a replacement graft in the manner described below. The suture 40 may comprise a plurality of parallel strands, although, in the preferred embodiment, a single strand folded on itself has been found sufficient depending on size. As will be understood below, the combination of the filamentous strand 40 with the features of the anchor member 12 can perform different functions at different points along the path 29 of the suture 40 through the apertures 20, 22 of the anchor member 12.

Figure 4:
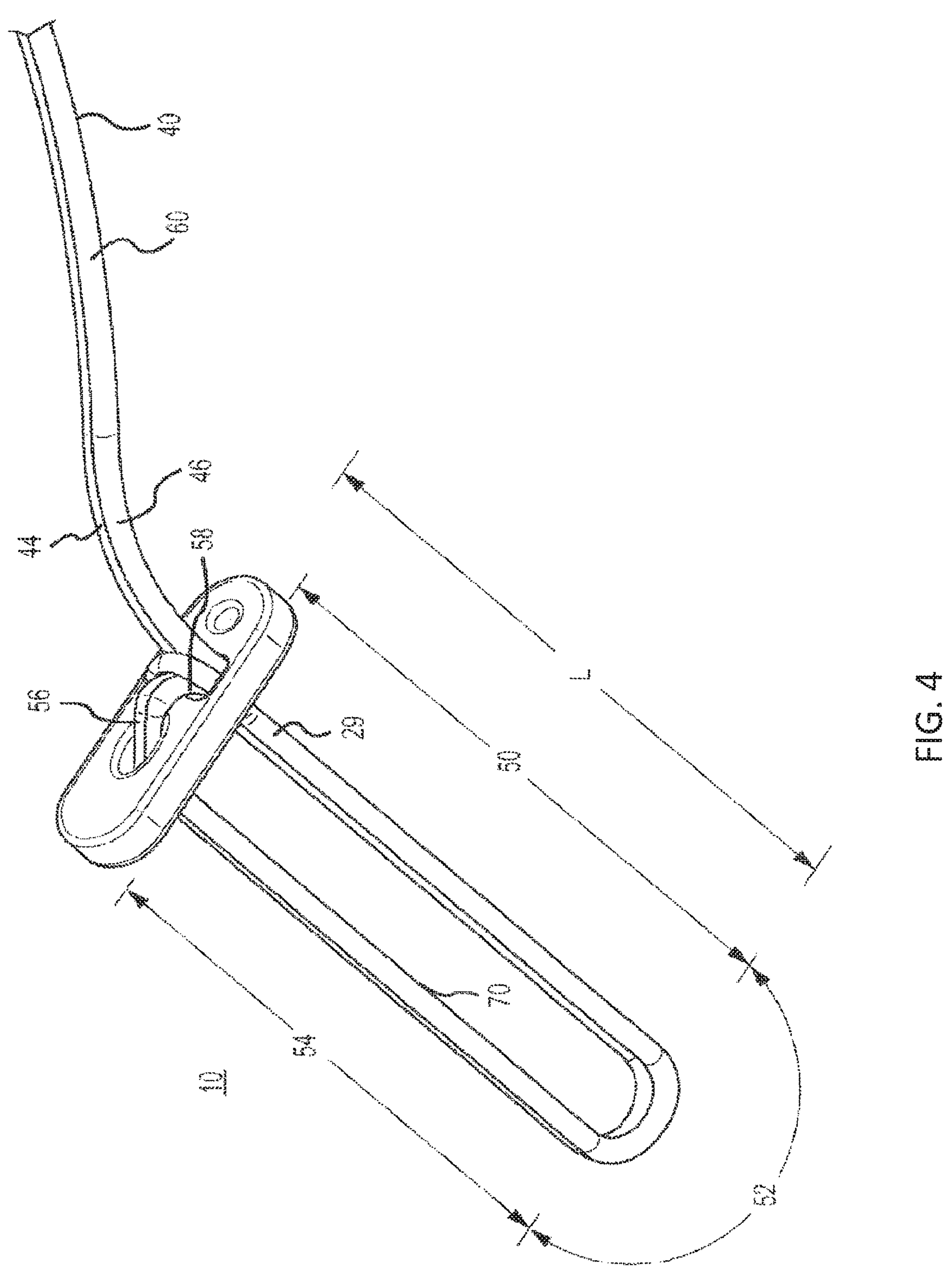
FIG. 4 is a side perspective view schematic representation of the anchor member of the suspensory graft fixation device of FIG. 3 with a suture, according to an embodiment.
Figure 5:
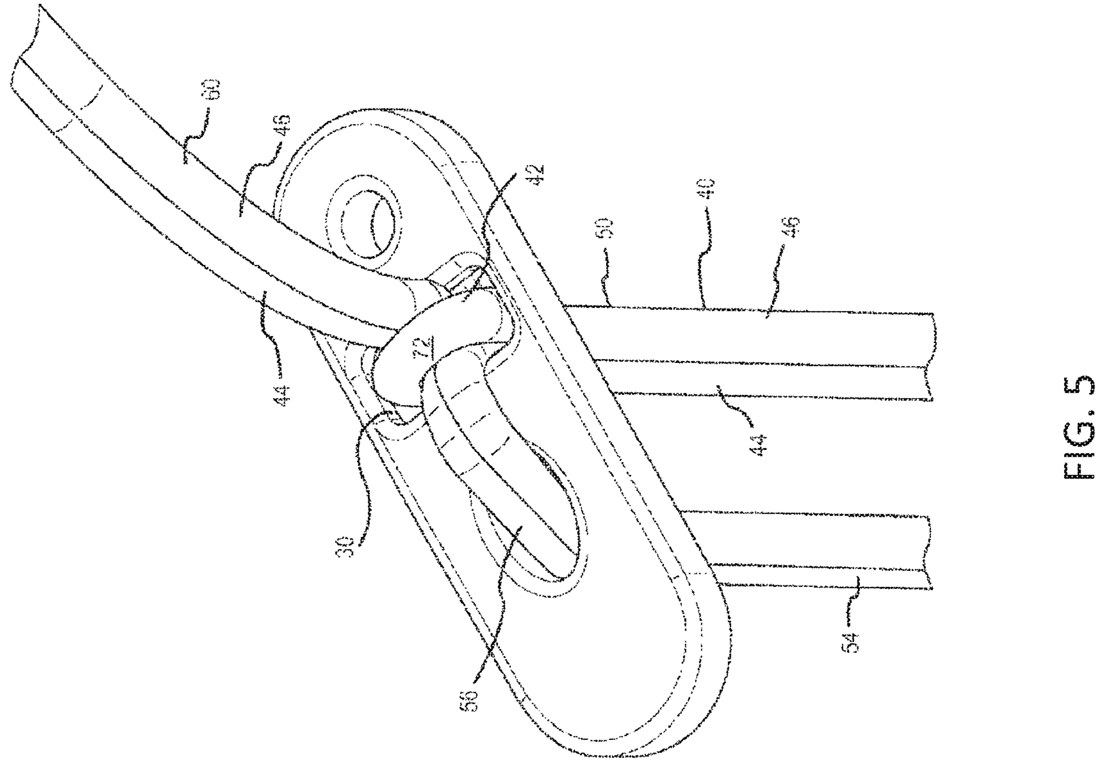
FIG. 5 is a close-up top perspective view schematic representation of the suspensory graft fixation device of FIG. 4, according to an embodiment.

To aid in describing an example winding path 29 of the suture strand 40, which in the preferred embodiment is a hollow-core suture, the suture strand 40 is first folded on itself to form a central bight portion 42, thus creating two limbs 44, 46 extending from the bight 42. Each limb has a length extending from the bight 42 to the free, unattached end of the limb 44, 46. Referring to FIG. 5, suture leg 44 is passed down through receiving aperture 20 into section 50, across the bottom of graft supporting loop 70 into section 52, up on the other side of loop 70 into section 54, up through aperture 34 into section 56, under bight 42 into section 58 and away from the anchor member 12 in section 60. Similarly, limb 46 of the suture follows a path parallel with that of limb 44 through the same sections as suture limb 44. Path 29 results in formation of locking loop 70, the length L (in FIG. 4) of which is easily adjustable. The loop is created by the suture following the path of sections 50, 52, 54, 56 and 58. Loop 70 is intended to receive a graft, generally folded on itself in the case of soft tissue (not shown) suspended from section 52.

In the preferred embodiment the two loop strands forming supporting loop 70 are made of high strength, filamentous material such as ultra-high molecular weight polyethylene and anchor member 12 is comprised of implantable grade titanium.

By design, the suspensory graft fixation device 10 allows for the activation of a loop length adjustment mechanism to resize the graft supporting loop 70 by applying tension to the construct in one direction (distally), and the activation of an automatic loop locking mechanism by applying tension to the construct in the opposite direction (proximally). In the preferred embodiment, the central bight 42 forms a locking loop 72 creating downward (as viewed in FIG. 5) pressure on the suture in section 58 due to the downward force exerted on supporting loop 70 by the graft itself (not shown) adjacent section 52. This portion of section 52 is sometimes referred to as a “saddle”. Locking loop 72 pushes the suture in section 58 deeper into the pocket/recess 30, thus activating the locking mechanism which causes the suture to engage the perimeter 32 and apertures 20, 22 thereby further increasing the friction created by locking loop 72.

Figure 3:
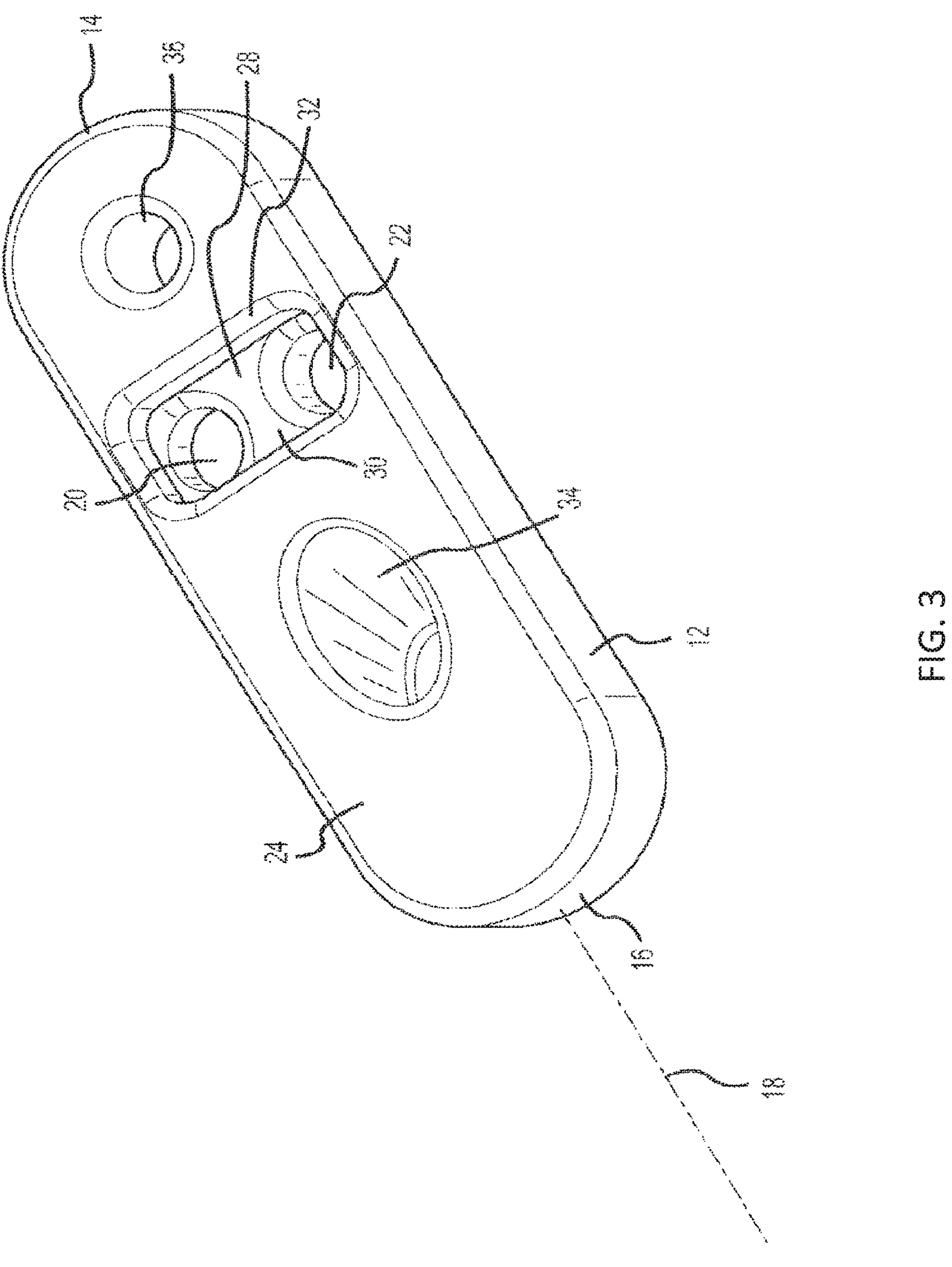
FIG. 3 is a perspective view schematic representation of an anchor member of a suspensory graft fixation device, according to an embodiment.
Figure 6:
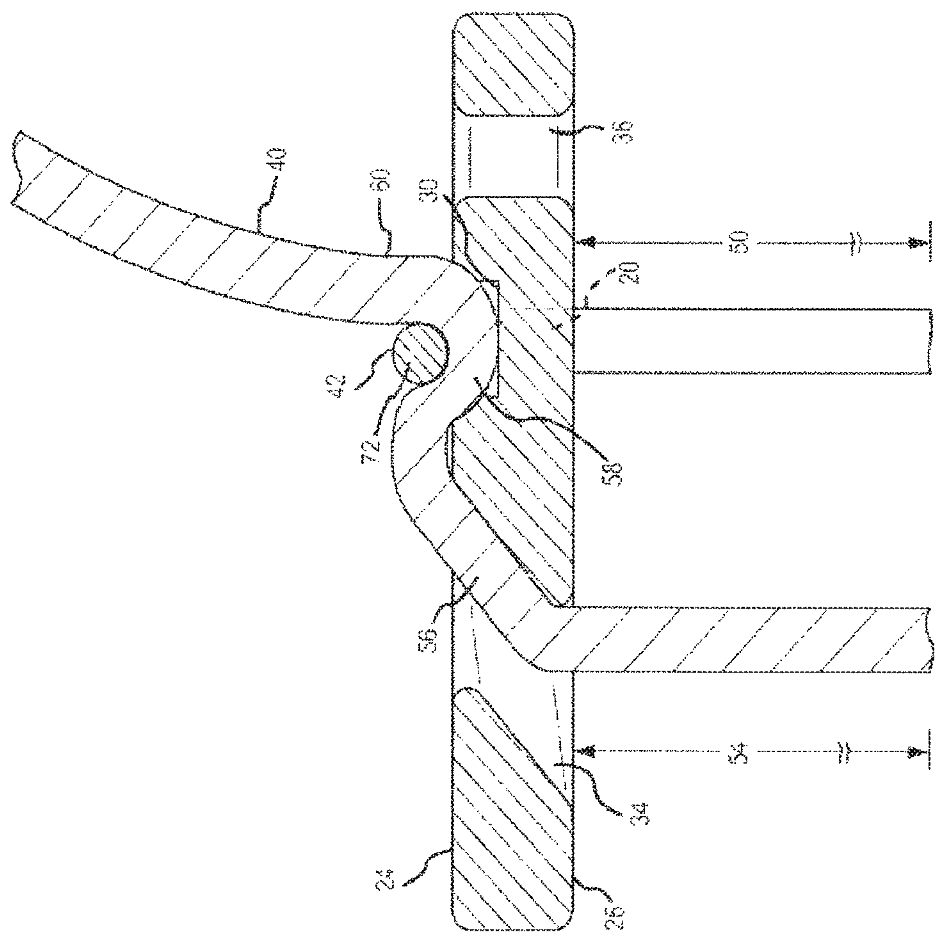
FIG. 6 is a cross-sectional view schematic representation of the suspensory graft fixation device of FIG. 5, according to an embodiment.

Adjustability of the loop length L (FIG. 4) is achieved by simply pulling on the filament limbs 44, 46 in section 60 in a distal direction away from anchor member 12. This type of action simultaneously decreases the size/length of the supporting loop 70 and releases the pressure being applied by locking loop 72. When the desired size/length of the supporting loop 70 is achieved, tension is placed on the graft supporting loop 70 in the opposite, proximal direction so the locking loop 72 automatically squeezes the suture limbs 44, 46 securely against anchor member 12 to lock the suture limbs 44, 46 in place. The locking of the graft supporting loop 70 is achieved due to the friction imparted on the filament ends by the locking loop 72. As best seen in FIGS. 3 and 6, aperture 34 is angled relative to surfaces 24 and 26, and inclined toward apertures 20 and 22. This arrangement has been found to enhance the friction between the suture and the surfaces and edges of the anchor member 12.

While the path of the preferred embodiment of device 10 is as described above, alternate embodiments are feasible. Thus, while the suture path through anchor member 12 results in device 10 comprising a graft supporting element in the form of the aforementioned graft supporting loop member 70 suspended from anchor member 12, alternate embodiments of suspensory graft fixation device 10 are feasible in which bridge 28 between suture receiving apertures 20 and 22, is formed by a transverse pin in the middle of a single opening (not shown). Such a structure would form a bridge and a pair of apertures on either side of the pin.

Another alternate embodiment could comprise a different loop construction than that described above. As shown in FIGS. 4 through 6, loop member 70 is formed from a single length of suture or other filamentous material 40. In an alternate embodiment the loop could be formed by a plurality of individual suture loops (not shown) which together form graft supporting loop 70. In yet another alternate embodiment, loop 70 may be made to pass through an optional slidable flexible cylindrical sleeve 40 (not shown) situated at the section 52 side of the supporting loop, opposite anchor member 12.

In yet another alternate embodiment, in order to facilitate orienting elongated anchor member 12 parallel to the bone tunnel axis and pulling it through the bone tunnel, an optional pulling-suture aperture 36 may be formed at the leading end of the anchor member 12. Ultimately, in operation, the suspensory graft fixation device 10 serves to enable adjustment of loop length L while also producing a relatively large graft fixation force.

In the preferred embodiment, the length of anchor member 12 may range from 12 mm to 20 mm, the diameters of apertures 20 and 22 may be on the order of 1 mm, the pocket/recess 30 may be in the range of 1 mm-2 mm wide and the suture diameter may be on the order of 1 mm or USP size #5.

Figure 7:
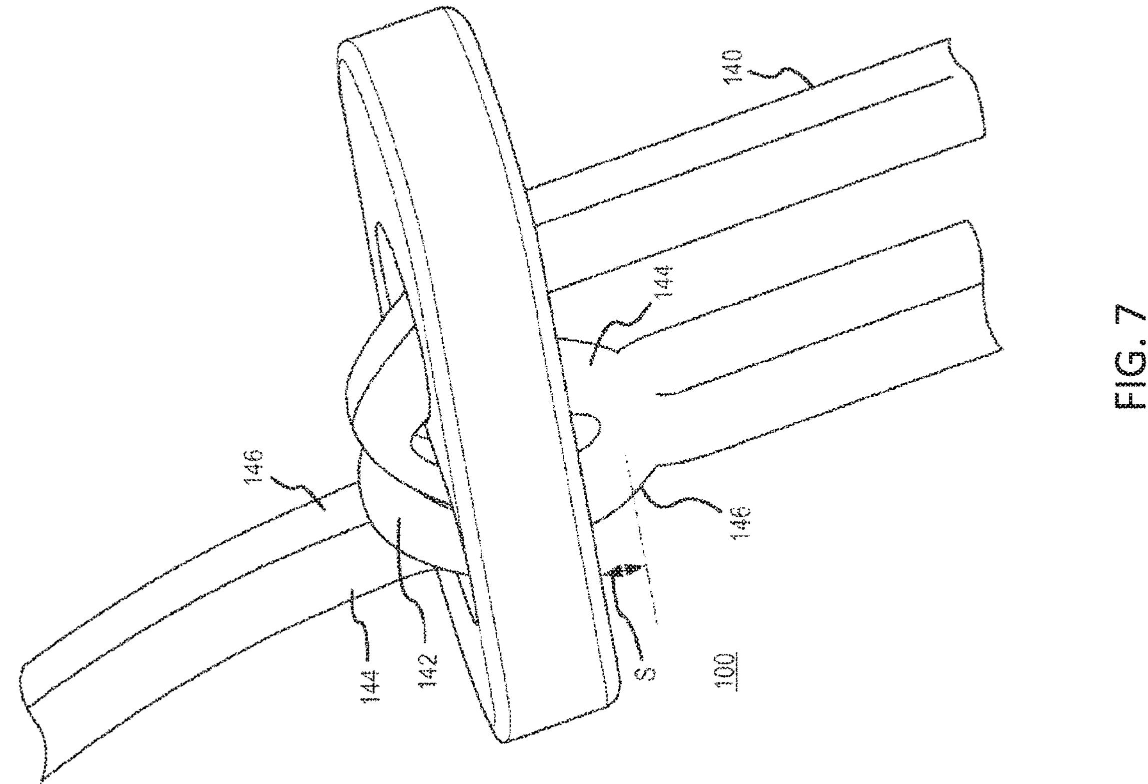
FIG. 7 is a side perspective view schematic representation of a suspensory graft fixation device, according to an alternative embodiment.

An alternate embodiment of the suspensory graft fixation device 10 of FIGS. 3-6 is shown in FIG. 7 as device 100. Device 100 comprises component parts identical to those of device 10 with the sole exception being that the structure of filamentous strand 140 is modified. That is, strand 140 is folded on itself to produce a bight 142 from which extend two limbs 144 and 146, however, one of these limbs is passed (e.g., via piercing) through the lumen of the other end. Alternatively, as shown in FIG. 7, as the two limbs are threaded through the suture receiving apertures (not seen in FIG. 7), at a point a short distance “S” below the anchor member, limb 144 passes through limb 146 and/or limb 146 passes through limb 144. This has the effect of loosely securing the strand 140 to device 100 to thereby limit travel of the bight 142 when ends 144 and 146 are momentarily pulled distally to resize the graft retaining loop.

Figure 8:
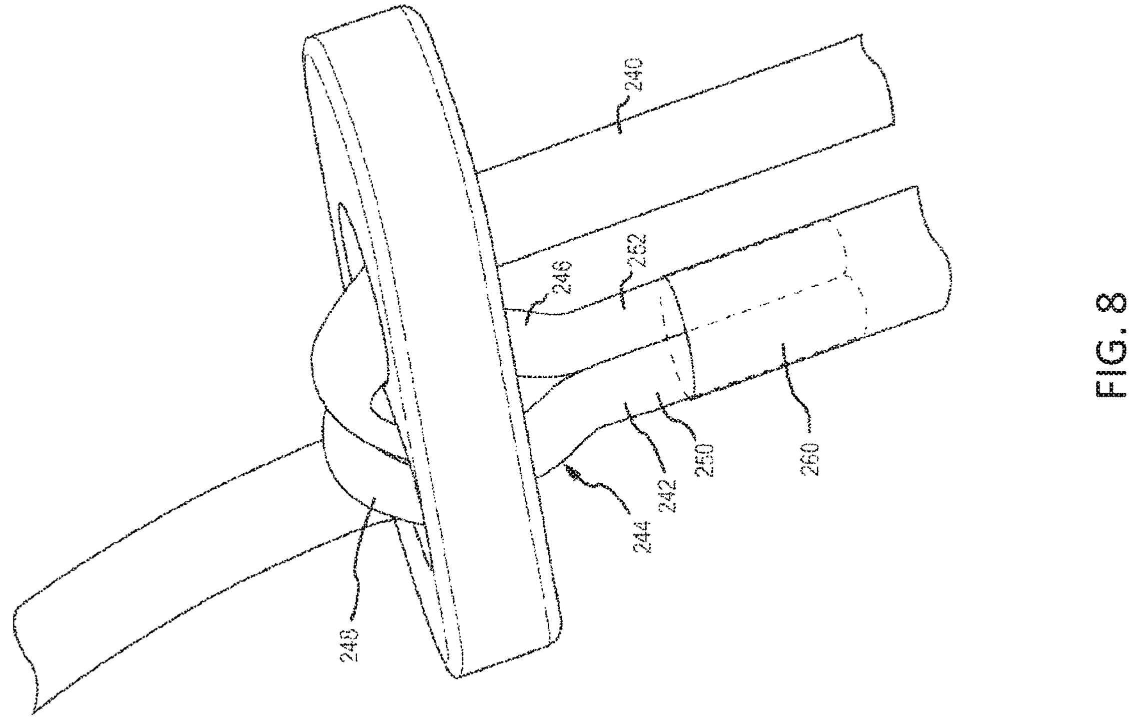
FIG. 8 is a side perspective view schematic representation of a suspensory graft fixation device, according to yet another embodiment.

The use of a single length of filamentous material folded on itself and directed in a winding path facilitates the construction and operation of device 10. In part, this is because the bight 42 creates a locking loop 72 due to the passage of the suture limbs 44, 46 under bight 42. It will be understood, however, that an alternate embodiment could be formed from a single strand 240 of a hollow core suture instead of double strands 44, 46, as shown in FIG. 8. In this case, a separate short strand 242 of suture is folded on itself to create a bight element 244 having only a loop 246, creating a locking loop 248, and a pair of very short limbs 250 and 252. The ends of the limbs 250, 252 of the short strand 242 are received a predetermined distance within the lumen 260 of the single hollow core suture 240. It will be understood that this construct operates like a “finger trap” wherein tension on the end of suture 240 will cause it to constrict around legs 250, 252.

Referring back to FIG. 1, the suspensory graft fixation device 10 of FIGS. 3-6 can be arranged in the organization device 300. In FIG. 1, the organization device 300 is in the open position. In the open position, the substrate 302 is substantially planar. The suspensory graft fixation device 10 is loaded onto the first side 308 of the organization device 300 when it is in the open position. As shown in FIG. 1, the supporting loop 70 of the suspensory graft fixation device 10 is wrapped around the first and second tabs 328, 330 and the intermediary tabs 340.

Specifically, as shown in FIG. 1, the supporting loop 70 is first wrapped around the open first tab 328 and the open second tab 330. Then, the supporting loop 70 is pulled through the two open intermediary tabs 340 such that the supporting loop 70 is maintained by the first and second tabs 328, 330 and intermediary tabs 340 in a triangular configuration, as shown. Further, the bottom 71 of the supporting loop 70 extends across the first opening 324 between the first tab 328 and the second tab 330. The bottom 71 of the supporting loop 70 extends across the opening 324 to facilitate placement of a soft tissue graft through the supporting loop 70.

Still referring to FIG. 1, the limbs 44, 46 of suture 40 extending from the elongated anchor member 12 are pulled toward the top edge 318 of the first panel 304. The limbs 44, 46 are pulled through the central top slit 336C in the top edge 318 of the first panel 304. Accordingly, the limbs 44, 46 extend approximately along the central longitudinal x-x axis. In this configuration of the suspensory graft fixation device 10, the elongated anchor member 12 is positioned between the first opening 324 (and intermediary tabs 340) and the central top slit 336C. In an embodiment, the elongated anchor member 12 extends approximately along the central longitudinal x-x axis.

To secure the elongated anchor member 12 in position, the limbs 44, 46 are wrapped from the central top slit 336C around one of the periphery top slits 336B. Thereafter, the limbs 44, 46 are pulled from that periphery top slit 336B through one of the bottom slits 338B. In the depicted embodiment, the limbs 44, 46 extend in a substantially straight line from the periphery top slit 336B to the bottom slit 338B. In an embodiment, the limbs 44, 46 are additionally passed through the second tab 330 when the limbs 44, 46 are pulled from the periphery top slit 336B to the bottom slit 336B (adjacent the second tab 330).

Optionally, a pulling suture 74 is passed through the pulling aperture 36 in the elongated anchor member 12. The pulling suture 74 is passed through the pulling aperture 36, creating two pulling limbs 76, 78. In the depicted embodiment, the pulling limbs 76, 78 extend from the elongated anchor member 12 toward the top edge 318 of the first panel 304. The pulling limbs 76, 78 are passed through the central top slit 336C (approximately along the central longitudinal x-x axis).

Thereafter, the pulling limbs 76, 78 are passed around one of the periphery top slits 336A. From the periphery top slit 336A, the pulling limbs 76, 78 extend to one of the bottom slits 338A. In the depicted embodiment, the pulling limbs 76, 78 extend in a substantially straight line from the periphery top slit 336A to the bottom slit 338A. In an embodiment, the pulling limbs 76, 78 are additionally passed through the first tab 328 when the limbs 44, 46 are pulled from the periphery top slit 336A to the bottom slit 338A (adjacent the first tab 328).

Alternative configurations and placement of the limbs 44, 46 and pulling limbs 76, 78 through the top slits 336 and bottom slits 338 can be used as long as the limbs 44, 46 and the pulling limbs 76, 78 are separately maintained and the tails (not shown) of both all of the limbs 44, 46 and the pulling limbs 76, 78 are on a second side (not shown) of the first panel 304. Wrapping of the limbs 44, 46 and pulling limbs 76, 78 into the top slits 336 and bottom slits 338 prevents entanglement during product transportation and storage.

Figure 2:
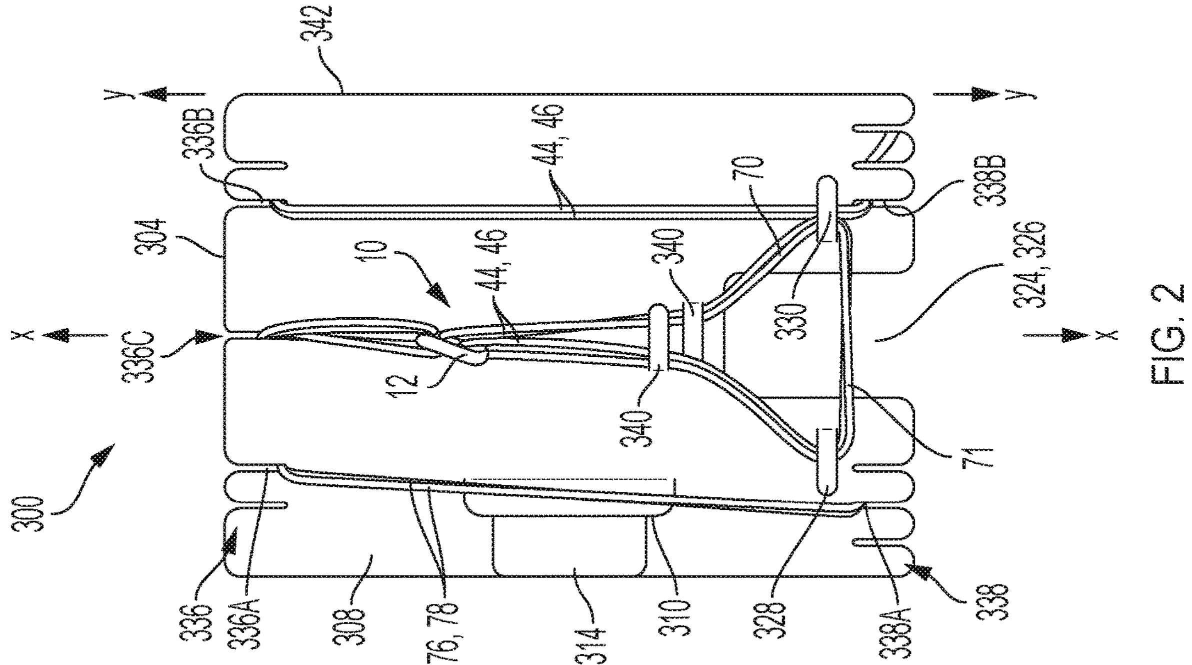
FIG. 2 is a perspective view schematic representation of an implant and suture organization device in a closed position, according to an embodiment.

Turning now to FIG. 2, there is shown a perspective view schematic representation of the implant and suture organization device 300 in a closed position, according to an embodiment. From the open position, shown in FIG. 1, the organization device 300 is foldable along the central longitudinal y-y axis to the closed position shown in FIG. 2. In the embodiment shown in FIG. 1, the substrate 302 comprises perforations 342 (slits or other cuts) along the central longitudinal y-y axis that allow the first panel 304 and the second panel 306 to fold relative to each other. In the embodiment depicted in FIG. 2, the first panel 304 can be symmetrical with the second panel 306 such that the first and second panels 304, 306 are substantially the same size and the first and second openings 324, 326 are substantially aligned (in the closed position).

From the open position shown in FIG. 1, the second panel 306 is rotated toward the first panel 304 (or vice versa) to the closed position, shown in FIG. 2. The second panel 306 covers the second side (not shown) of the first panel 304, enclosing the tails (not shown) of the pulling limbs 76, 78 and limbs 44, 46 therebetween. The pulling limbs 76, 78 and limbs 44, 46 are closed within the panels 304, 306 to prevent inadvertent contamination of the sutures 40 upon removal from sterile barrier. To maintain the closed position, the protrusion 314 in the side 316 of the second panel 306 is extended through the locking slit 310 in the first panel 304, as shown in FIG. 2.

Turning now to FIGS. 9-13, there are shown various view schematic representations of an alternative exemplary embodiment of an implant with suture. In the embodiment shown in FIGS. 9-13, the implant (and suture) is a suspensory graft fixation device 1100, such as that taught in PCT/US18/49698 filed on Sep. 6, 2018, and incorporated herein by reference. Other implants with sutures (as should be understood by a person of ordinary skill in the art in conjunction with a review of this disclosure) can be used in conjunction with the organization device 300.

Figure 9:
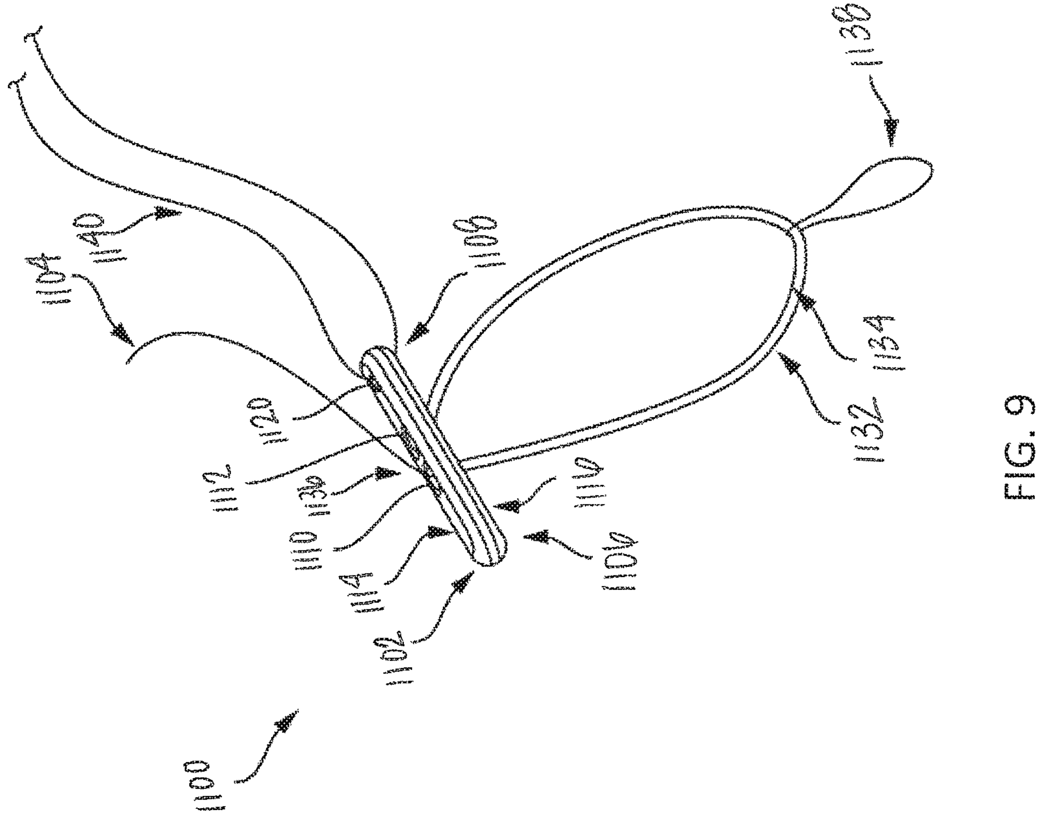
FIG. 9 is a perspective view schematic representation of a suspensory fixation device, according to an alternative embodiment.

FIG. 9 shows a side perspective view schematic representation of a suspensory graft fixation device 1100, according to an embodiment. The device 1100 comprises an elongated anchor member 1102 and a length of suture 1104. In the depicted embodiment, the suture 1104 is in the form of a filamentous strand composed of high strength, filamentous material such as ultra-high molecular weight polyethylene. The anchor member 102 can be composed of metal, such as implantable grade titanium, or any other suitable bioabsorbable or biocompatible material (as should be understood by a person of ordinary skill in the art in conjunction with a review of this disclosure). In embodiments, the length of anchor member 1102 may range from 12 mm to 20 mm.

Figure 10:
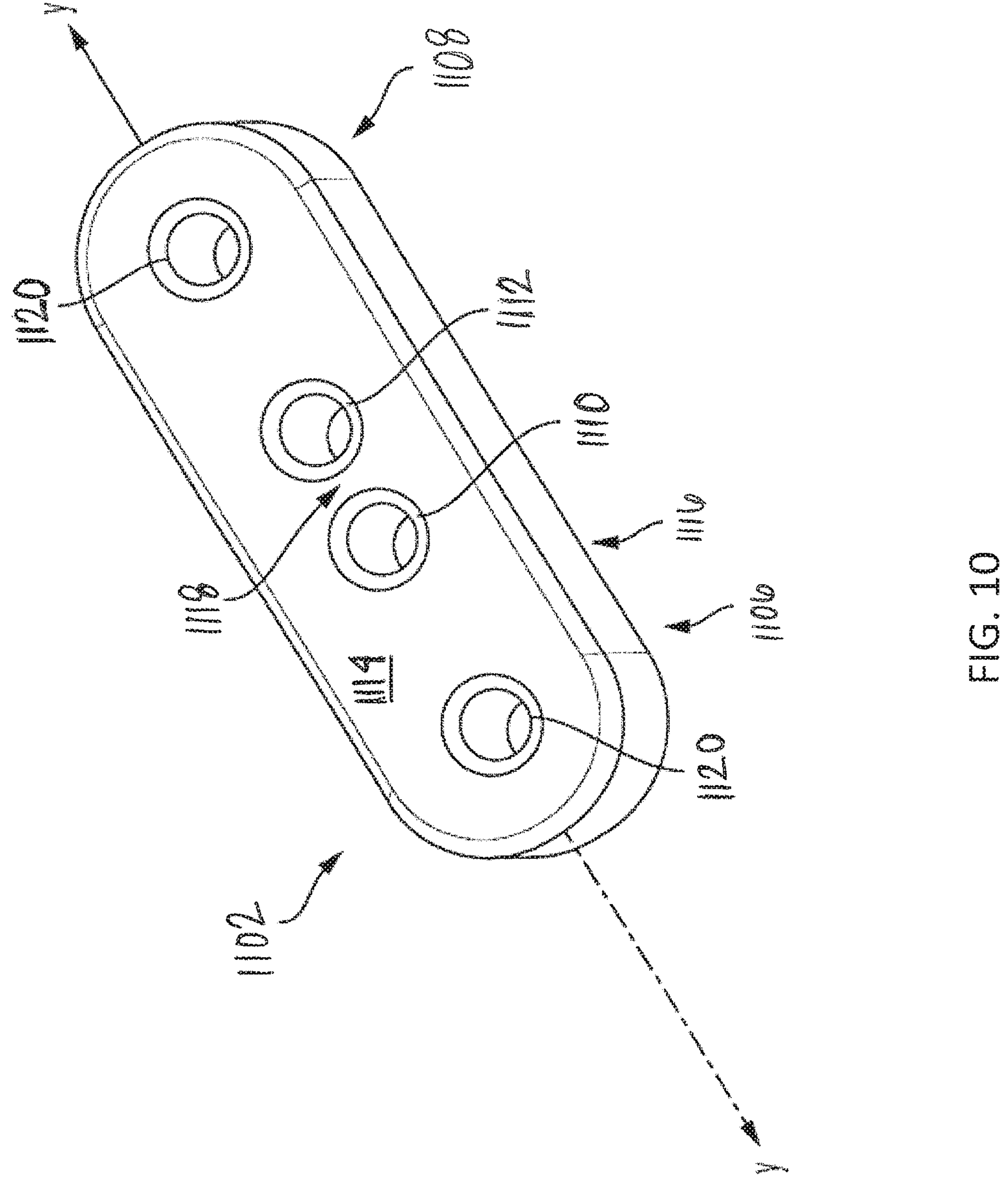
FIG. 10 is a top perspective view schematic representation of the anchor member of the suspensory fixation device, according to an alternative embodiment.

FIG. 10 shows a top perspective view schematic representation of the anchor member 1102 of the suspensory fixation device 1100, according to an embodiment. The anchor member 1102 extends along a central longitudinal y-y axis between its first end 1106 and second end 1108. The anchor member 1102 also has a pair of central suture receiving apertures 1110, 1112, which are sized or otherwise configured to receive suture 1104 that will form loops. For example, the diameters of suture receiving apertures 1110, 1112 may be on the order of 1 mm, while the diameter of the suture 1104 may be on the order of 1 mm or USP size #5. In an embodiment according to FIG. 13, the anchor member 1102 is oblong in geometry. In particular, as shown, a length L of the anchor member 1102 is greater than a width w of the anchor member 1102. The oblong geometry of the anchor member 1102 allows the anchor member 1102 to pass through narrow bone tunnels.

Figure 11:
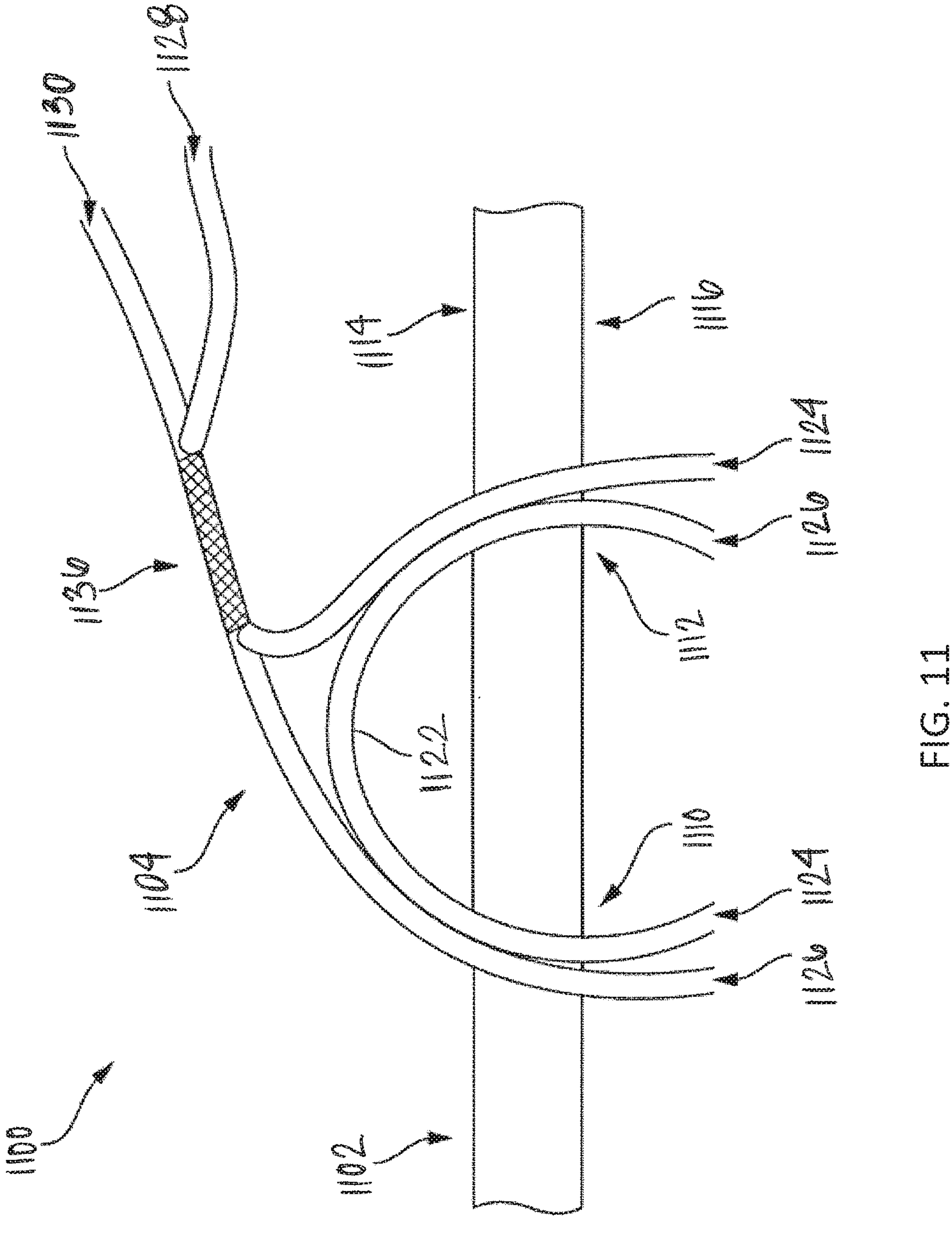
FIG. 11 is a cross-sectional side view schematic representation of the suspensory fixation device, according to an alternative embodiment.
Figure 12:
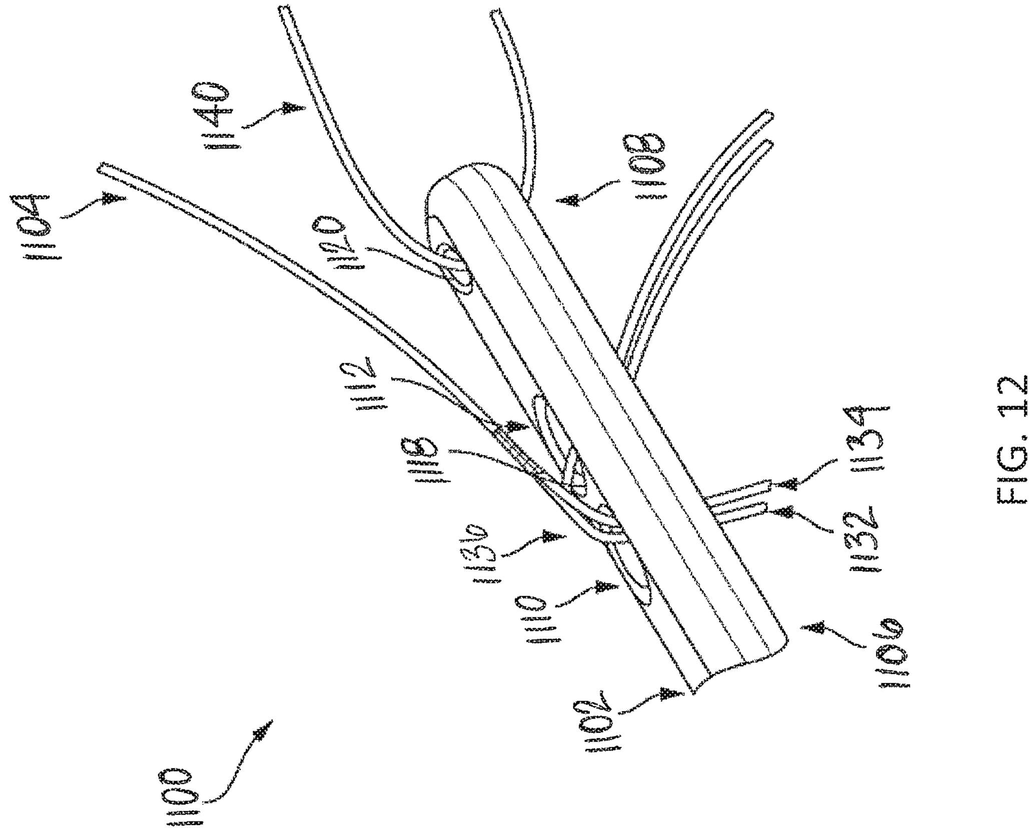
FIG. 12 is a close-up perspective view schematic representation of a suspensory fixation device, according to an alternative embodiment.
Figure 13:
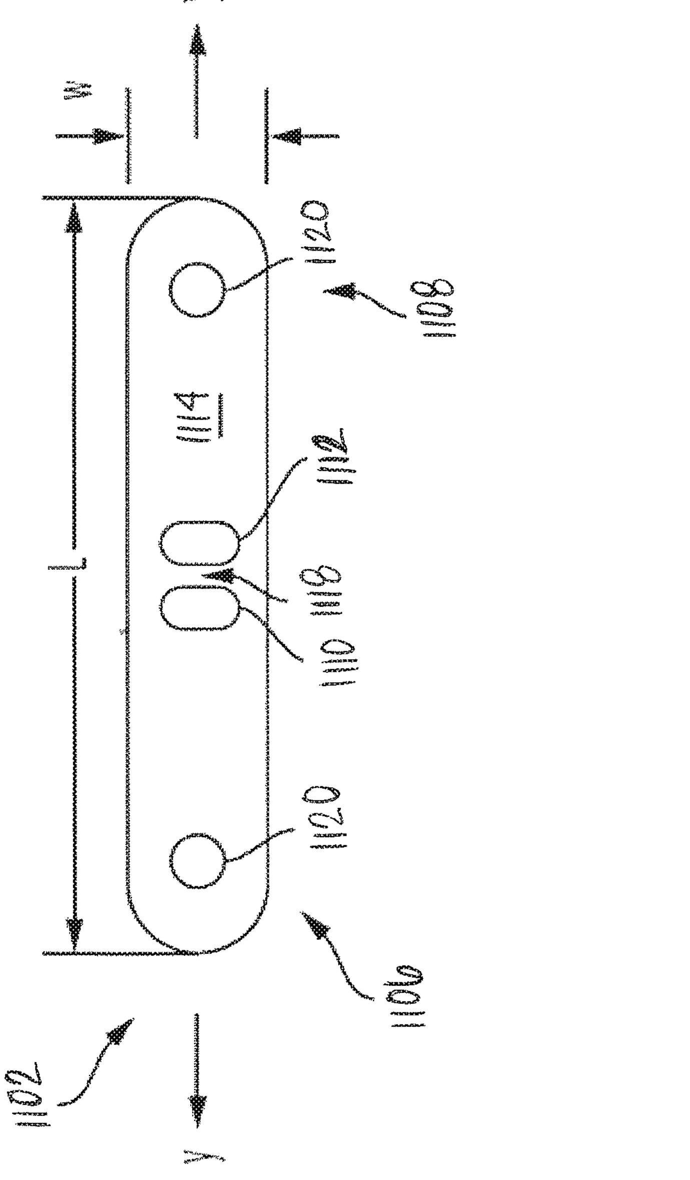
FIG. 13 is a top view schematic representation of a suspensory fixation device, according to an alternative embodiment.

Referring back to FIG. 10, the anchor member 1102 has a top surface 1114 and a bottom surface 1116 (best seen in FIGS. 11-12). The bottom surface 1116 is sometimes referred to as the proximal surface and is intended to be placed adjacent a bone tunnel exit. As used herein, the term "proximal" refers to the side of the bone containing the bone tunnel (i.e., extending inwardly away from the surface of the lateral femur in an ACL procedure), and the term "distal" refers to the side of the bone against which the transverse anchor member 1102 rests (i.e., extending outwardly away from the surface on the lateral femur).

Still referring to FIG. 10, the suture receiving apertures 1110, 1112 are situated on opposite sides of a central bridge portion 1118 extending between them. The anchor member 1102 may also optionally have one or more placement apertures 1120 extending between the top and bottom surfaces 1114, 1116. In the depicted embodiment, there is a placement aperture 1120 at the first end 1106 of the anchor member 1102 and a placement aperture 1120 at the second end 1108 of the anchor member 1102. The placement apertures 1120 are sized or otherwise configured to receive a placement suture 140 (or another filamentous strand) to facilitate placement of the device 1100 at a bone tunnel exit. For example, a placement suture 1140 is attached to a placement aperture 1120 and pulled through the bone tunnel, facilitating orienting the elongated anchor member 1102 parallel to the bone tunnel axis.

As shown in FIG. 9, the suspensory fixation device 1100 is designed to have the anchor member 1102 operate with a filamentous strand 1104 suitable for following a tortuous path through the suture receiving apertures 1110, 1112 of anchor member 1102. In an embodiment, the filamentous strand 1104 is a single length of appropriately sized suture. The term "suture" as used herein may be used interchangeably with "filamentous material" and, as described above, will be understood to mean any biocompatible or bioabsorbable strand of material which can, when combined with anchor member 1102, operate to support a replacement graft in the manner described below. As will be understood below, the combination of filamentous strand 1104 with the features of anchor member 1102 can perform different functions along the path of the suture 104 through the suture receiving apertures 1110, 1112 of the anchor member 1102.

Referring now to FIG. 11, there is a cross-sectional side view schematic representation of the suspensory fixation device 1100, according to an embodiment. To load the anchor member 1102 shown in FIG. 10, the filamentous strand 1104 is passed or wrapped through the suture receiving apertures 1110, 1112. Specifically, as shown in FIG. 11, the filamentous strand 1104 is first folded on itself to form a central bight portion 1122, thus creating two limbs 1124, 1126 extending from the central bight portion 1122. Each limb 1124, 1126 has a length extending from the central bight portion 1122 to the free, unattached ends 1128, 1130 of the limbs 1124, 1126.

Still referring to FIG. 11, the first limb 1124 is passed through a first suture receiving aperture 1110 and the second limb 1126 is passed through a second suture receiving aperture 1112 (in the downward direction as shown in FIG. 11). The first and second limbs 1124, 1126 extend through the suture receiving apertures 1110, 1112 from the top surface 1114 of the anchor member 1102 to the bottom surface 1116 of the anchor member 1102. The second limb 1126 is then passed up through the first suture receiving aperture 1110 from the bottom surface 1116 of the anchor member 1102 to the top surface 1114 of the anchor member 1102. Similarly, the first limb 1124 is passed up through the second suture receiving aperture 1112 from the bottom surface 1116 of the anchor member 1102 to the top surface 1114 of the anchor member 1102. As shown in FIGS. 9 and 11, the central bight portion 1122 extends over the central bridge portion 1118 on the top surface 1114 of the anchor member 1102, while two adjustable loops 1132, 1134 extend from the suture receiving apertures 1110, 1112 through the bottom surface 1116 of the anchor member 1102.

With the free, unattached ends 1128, 1130 extending from the top surface 1114 of the anchor member 1102, a splice 1136 is created in the second limb 1126, as shown in FIG. 11. The first limb 1124 is passed through the splice 1136, forming a jacket around the first limb 1124. In the depicted embodiment, the splice 1136 is adjacent and above (distal to) the central bight portion 1122. With the filamentous strand 1104 wrapped through the suture receiving apertures 1110, 1112, creating adjustable loops 1132, 1134 extending from the bottom surface 1116 of the anchor member 1102, and the splice 1136 extending from the top surface 1114 of the anchor member 1102, the device 1100 can be used to adjustably apply and release tension on a graft at a bone tunnel exit.

While the suture path of an embodiment of device 1100 is as shown in FIG. 11, alternate embodiments are feasible. Thus, while the suture path through the anchor member 1102 results in device 1100 comprising a graft supporting element in the form of two adjustable loops 1132, 1134, there can be different loop constructions than that described above. For example, the adjustable loops 1132, 1134 are formed from a single length of suture 1104 (or other filamentous material) but in an alternate embodiment, the adjustable loops 1132, 1134 could be formed by a plurality of individual lengths of suture 1104 which together form the adjustable loops 1132, 1134.

In an embodiment, a placement suture 1140 is threaded through a placement aperture 1120 of the anchor member 1102. In use, the placement suture 1140 is inserted through a proximal end of a bone tunnel and pulled toward a distal end of the bone tunnel. The placement suture 1140 is pulled or otherwise tensioned toward the distal end of the bone tunnel, facilitating orienting the elongated anchor member 1102 substantially parallel to the bone tunnel axis while a graft attached to the second loop 1134 remains within the bone tunnel.

Figure 14:
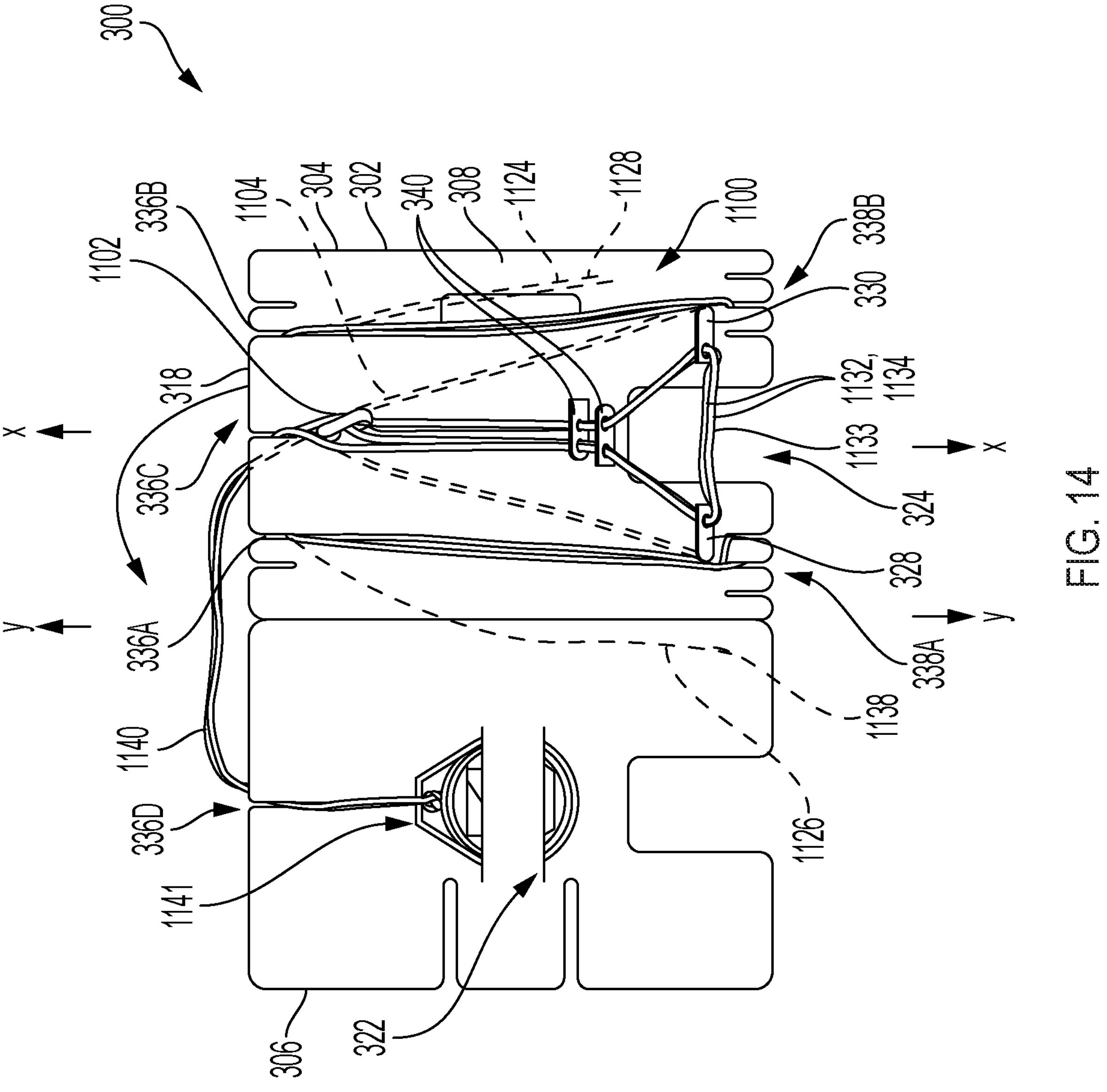
FIG. 14 is a perspective view schematic representation of an implant and suture organization device in an open position, according to an alternative embodiment.
Figure 15:
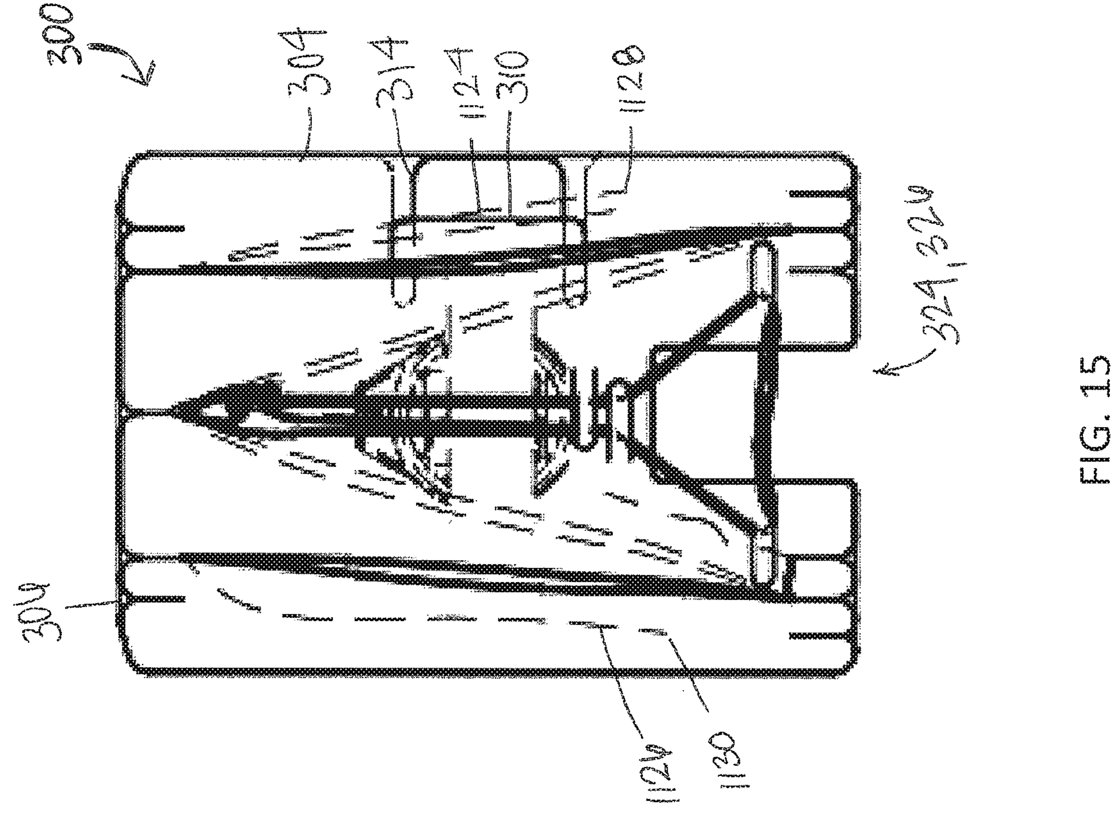
FIG. 15 is a perspective view schematic representation of an implant and suture organization device in a closed position, according to an alternative embodiment.

Referring now to FIGS. 14-15, there are shown perspective view schematic representation of the suspensory graft fixation device 1100 of FIGS. 9-13 installed on the suture organization device 300. In FIG. 14, the organization device 300 is in the open position. In the open position, the substrate 302 is substantially planar. The suspensory graft fixation device 1100 is loaded onto the first side 308 of the organization device 300 when it is in the open position.

As shown in FIG. 14, the adjustable loops 1132, 1134 of the suspensory graft fixation device 1100 are wrapped around the first and second tabs 328, 330 and the intermediary tabs 340. Specifically, the adjustable loops 1132, 1134 are first wrapped around the open first tab 328 and the open second tab 330. Then, the adjustable loops 1132, 1134 are pulled through the two open intermediary tabs 340 such that the adjustable loops 1132, 1134 are maintained by the first and second tabs 328, 330 and intermediary tabs 340 in a triangular configuration, as shown. Further, the bottoms 1133 of the adjustable loops 1132, 1134 extend across the first opening 324 between the first tab 328 and the second tab 330. The bottoms 1133 of the adjustable loops 1132, 1134 extend across the opening 324 to facilitate placement of a soft tissue graft through the adjustable loops 1132, 1134.

Still referring to FIG. 14, the limbs 1124, 1126 of suture 1104 extending from the elongated anchor member 1102 are pulled toward the top edge 318 of the first panel 304. The limbs 1124, 1126 are pulled through the central top slit 336C in the top edge 318 of the first panel 304. Accordingly, the limbs 1124, 1126 extend approximately along the central longitudinal x-x axis. In this configuration of the suspensory graft fixation device 1100, the elongated anchor member 1102 is positioned between the first opening 324 (and intermediary tabs 340) and the central top slit 336C. In an embodiment, the elongated anchor member 1102 extends approximately along the central longitudinal x-x axis.

To secure the elongated anchor member 1102 in position, the limbs 1124, 1126 are wrapped from the central top slit 336C around the periphery top slits 336A, 336B. Thereafter, the limbs 1124, 1126 are pulled from their respective periphery top slits 336A, 336B through the bottom slits 338A, 338B. In the depicted embodiment, the limbs 1124, 1126 extend in a substantially straight line from their respective periphery top slits 336A, 336B to bottom slits 338A, 338B.

Optionally, the placement suture 1140 passing through the placement aperture 1120 extends from the elongated anchor member 1102 toward the top edge 318 of the first panel 304. The placement suture 1140 is passed through the central top slit 336C (approximately along the central longitudinal x-x axis). Thereafter, the placement suture 1140 is passed over to the second panel 306. The placement suture 1140 is then passed through a central top slit 336D in the second panel 306. From the central top slit 336D, the placement suture 1140 extends to the retainer band 322. In the embodiment shown in FIG. 14, the placement suture 1140 is connected to a pull tab 1141. The pull tab 1141 is a device or other attachment connected to the placement suture 1140. When the pull tab 1141 is pulled, the adjustable loops 1132, 1134 are enlarged. In FIG. 14, the pull tab 1141 is placed and stored within the retainer band 322.

Alternative configurations and placement of the limbs 1124, 1126 and the placement suture 140 through the top slits 336 and bottom slits 338 can be used as long as the limbs 1124, 1126 and the placement suture 140 are separately maintained and the tails (not shown) of both all of the limbs 1124, 1126 and the placement suture 140 are on a second side (not shown) of the first panel 304. Wrapping of the limbs 1124, 1126 and the placement suture 1140 into the top slits 336 and bottom slits 338 prevents entanglement during product transportation and storage.

Turning now to FIG. 15, there is shown a perspective view schematic representation of the implant and suture organization device 300 of FIG. 14 in a closed position. From the open position, shown in FIG. 14, the organization device 300 is foldable along the central longitudinal y-y axis to the closed position shown in FIG. 15. In the embodiment depicted in FIG. 15, the first panel 304 can be symmetrical with the second panel 306 such that the first and second panels 304, 306 are substantially the same size and the first and second openings 324, 326 are substantially aligned (in the closed position).

From the open position shown in FIG. 14, the second panel 306 is rotated toward the first panel 304 (or vice versa) to the closed position, shown in FIG. 15. The second panel 306 covers the second side (not shown) of the first panel 304, enclosing the limbs 1124, 1126 (and their free, unattached ends 1128, 1130) therebetween. The limbs 1124, 1136 (and their free, unattached ends 1128, 1130) are closed within the panels 304, 306 to prevent inadvertent contamination of the sutures 1104 upon removal from sterile barrier. To maintain the closed position, the protrusion 314 in the side 316 of the second panel 306 is extended through the locking slit 310 in the first panel 304, as shown in FIG. 15.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A method for securing a suspensory graft fixation device in an organized configuration, comprising the steps of:

providing an organization device comprising a substrate having a top edge and a bottom edge with a first panel and a second panel extending therebetween, a central longitudinal axis, a first opening extending through the bottom edge and into the first panel, a first tab on the first panel adjacent a first side of the first opening, a second tab on the first panel adjacent a second side of the first opening, and one or more intermediary tabs in the first panel between the opening and the top edge;

providing a suspensory graft fixation device having an anchor body with a suture woven therethrough, creating a loop extending from a side of the anchor body and two limbs extending from an opposing side of the anchor body;

wrapping the loop around the first tab and the second tab such that a bottom of the loop extends across the first opening;

pulling the two limbs to and through the central top slit; and wrapping the two limbs from the central top slit to and through one of a plurality of top slits extending into the top edge of the first panel, and one of a plurality of bottom slits extending into the bottom edge of the first panel.

2. The method of claim 1, further comprising the step of folding the substrate along the central longitudinal axis such that the second panel rotates toward the first panel.

3. The method of claim 2, wherein the organization device comprises a spaced pair of cutouts in a side of the second panel, creating a protrusion, and a slit in the first panel extending between the top edge and the bottom edge.

4. The method of claim 3, wherein the step of folding the substrate along the central longitudinal axis such that the second panel rotates toward the first panel includes the step of extending the protrusion of the second panel into the slit of the first panel.

5. The method of claim 2, wherein the organization device comprises a retainer band on the second panel.

6. The method of claim 5, wherein the retainer band is formed from a pair of parallel slits in the second panel.

* * * * *